United States Patent [19]
Gibson

[11] 3,971,381
[45] July 27, 1976

[54] LAPAROTOMY SPONGE
[75] Inventor: Robert T. Gibson, Andrews, N.C.
[73] Assignee: Professional Surgical Manufacturing Company, Marietta, Ga.
[22] Filed: Feb. 19, 1975
[21] Appl. No.: 551,134

[52] U.S. Cl. ............................... 128/296; 128/156
[51] Int. Cl.² .................. A61F 15/00; A61F 13/00
[58] Field of Search .............. 128/156, 296, 290 R, 128/292; 428/134, 137

[56] References Cited
UNITED STATES PATENTS

| | | |
|---|---|---|
| 2,805,664 | 9/1957 | Heffernan ............................ 128/296 |
| 2,928,389 | 3/1960 | Ganz et al. ........................... 128/156 |
| 3,053,252 | 9/1962 | Wolf .................................... 128/156 |
| 3,308,488 | 3/1967 | Shoonman ...................... 128/296 X |
| 3,416,526 | 12/1968 | Yeremian ............................ 128/156 |
| 3,434,472 | 3/1969 | Herniman et al. .................. 128/156 |

Primary Examiner—Aldrich F. Medbery
Attorney, Agent, or Firm—Newton, Hopkins & Ormsby

[57] ABSTRACT

A laparotomy sponge is disclosed having a central ply of rayon and polypropylene sandwiched between two piles of gauze.

6 Claims, 6 Drawing Figures

LAPAROTOMY SPONGE

BACKGROUND OF THE INVENTION

Laparotomy sponges, pads, dressings and the like have heretofore typically comprised absorbent filler material such as cotton or rayon enveloped in woven gauze. U.S. Pat. Nos. 2,616,428, 2,829,648, 2,926,667 and 3,589,367 exemplify such sponges. Though these prior art materials have functioned satisfactorily, their performance has been significantly less than ideal. For example, where the sponge has a high content of good absorbent materials such as fibrous cotton, its strength is insufficient for retention of sound structural integrity when wetted. Conversely, where structural integrity of the pad has been enhanced through the use of binders or a relatively high content of woven gauze, the resulting loss in absorbency necessitates frequent sponge changes. This dilemna has heretofore eluded solution without creation of commercially unacceptable increases in manufacturing cost. Laparotomy sponges having absorbent material stitched or bonded together by adhesive at close intervals exemplify such high cost types.

Accordingly, it is a general object of the present invention to provide an improved laparotomy sponge.

More specifically, it is an object of the present invention to provide a laparotomy sponge capable of economical production having good fluid absorbency as well as good tensile strength.

Another object of the invention is to provide a laparotomy sponge which does not necessarily require the use of chemical binders.

Yet another object of the invention is to provide a laparotomy sponge which in use dispenses minimal lint.

SUMMARY OF THE INVENTION

In one preferred form of the invention a laparotomy sponge is provided having a central ply of rayon and polypropylene sandwiched between two plies of gauze.

In another form of the invention a laparotomy sponge is provided comprising a filler of mixed rayon and polypropylene fibers bonded together in a ratio of approximately 80% rayon and 20% polypropylene and shaped into a configuration having opposed waffled surfaces. The filler is covered with a gauze.

DESCRIPTION OF THE EXEMPLARY EMBODIMENT

Figure 1:
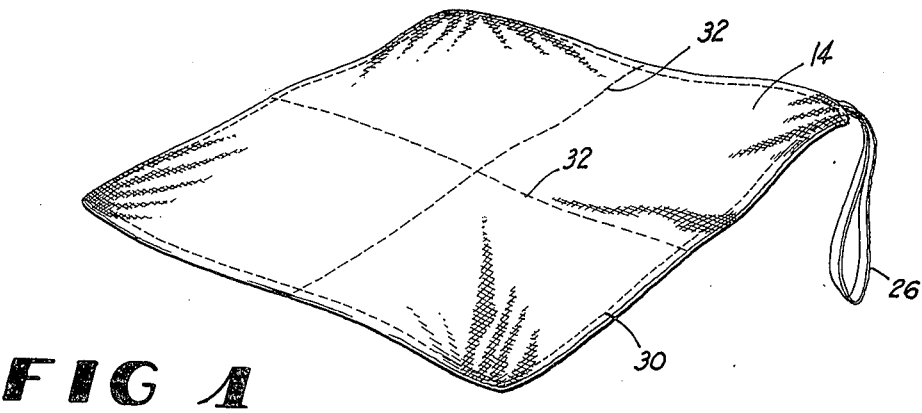
FIG. 1 is a perspective view of a laparotomy sponge embodying principles of the invention in a preferred form.
Figure 2:
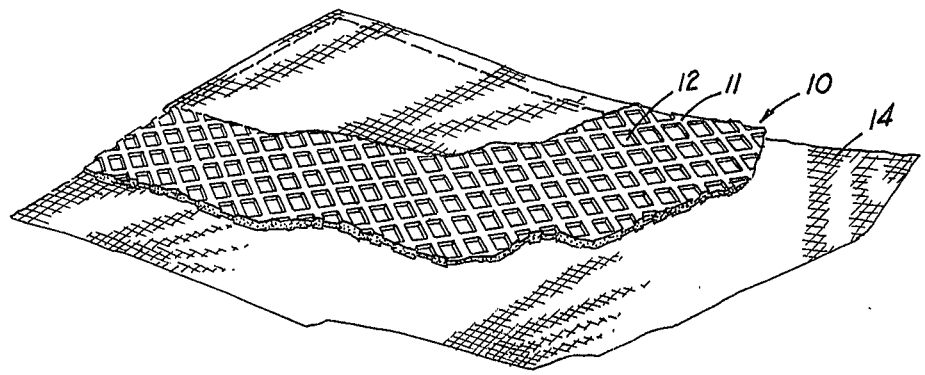
FIG. 2 is a perspective view of a portion of the laparotomy sponge shown in FIG. 1 with a strip of the sponge cover shown broken away to reveal filler material therebeneath.
Figure 3:
FIG. 3 is a transverse view in cross-section of the laparotomy sponge shown in FIGS. 1 and 2.
Figure 4:
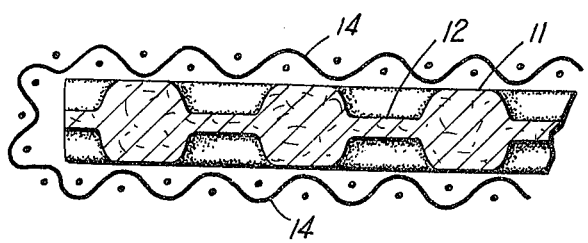
FIG. 4 is an enlarged cross-sectional view of an edge portion of the laparotomy sponge shown in FIGS. 1–3.
Figure 6:
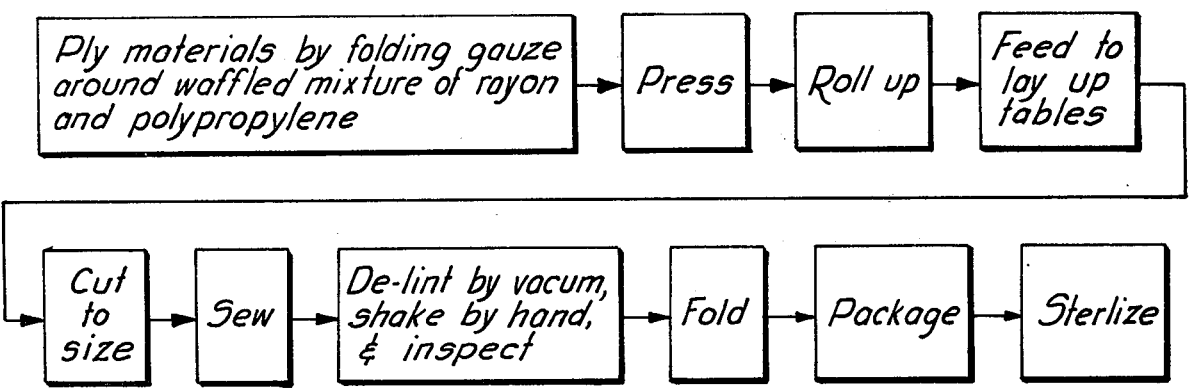
FIG. 6 is a block diagram illustrating a sequence of steps taken in forming the laparotomy sponge depicted in the other figures of which the first three are also schematically illustrated in FIG. 5.
Figure 5:
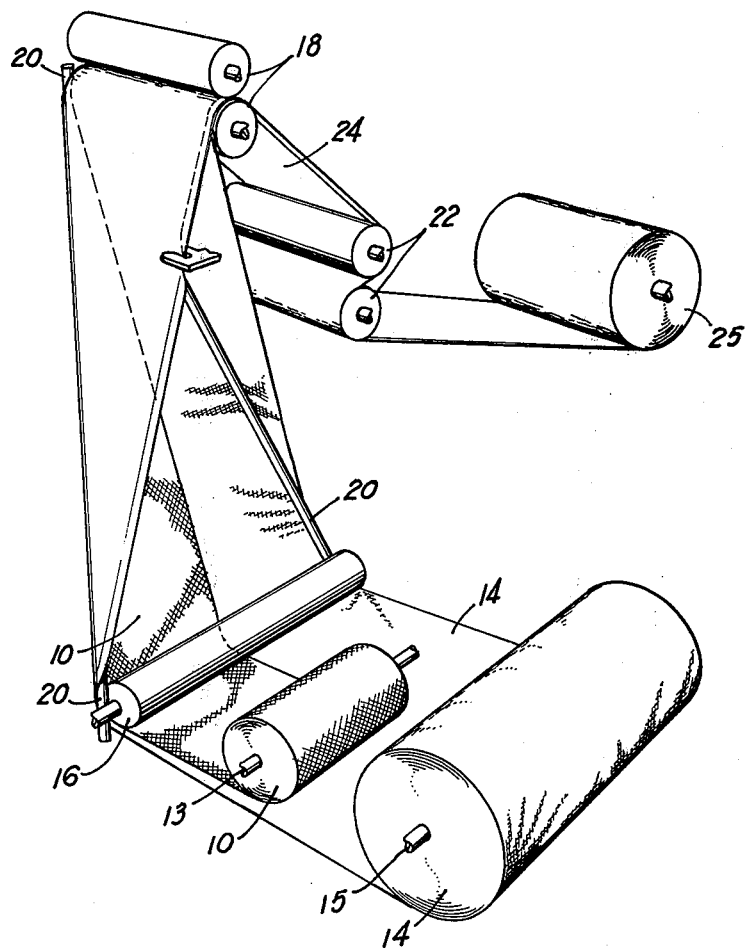
FIG. 5 is a schematic view of process equipment being used in forming the laparotomy sponge depicted in FIGS. 1–4.

In fabricating the laparotomy sponge depicted in the drawing, the filler material 10 is formed by mixing rayon fibers with polypropylene fibers in a preferred weight ratio of approximately 80% rayon to 20% polypropylene. The resulting mixture is pressed into a batt and heat bonded. A knurled roll is then passed over opposing surfaces of the batt to form opposing waffled surfaces in a diamond pattern of alternate raised and depressed areas 11 and 12. The resultant filler material is then rolled onto a spindle 13, and has a preferred weight range of 45–55 grams per square yard.

Next, a roll of gauze 14 or other suitable foraminous material is provided having a width slightly greater than double the width of the filler. Preferably, the gauze is formed of white cotton having from 24 to 28 threads per inch warp and 20 to 24 threads per inch filling and weighing between 23 and 27 grams per linear yard. The gauze is provided on a spindle 15 from which it is unwound and passed in laterally offset relation beneath the roll of filler material 10. The filler is thus seen to partially overlay the gauze being unwound from spindle 15. The resulting two plies are then passed beneath a first roller 16 and then upwardly between a pair of rollers 18. In passing between roller 16 and rollers 18 the material is plough folded so that the side edges of the gauze are brought together. In accomplishing this a pair of guide bars 20 are provided between the rollers with their lower ends straddling roller 16 but with their upper ends located together to one side of upper rollers 18. In extending between the lower and the upper rollers the guide bar thus serves to introduce a quarter turn plough twist to that portion of the gauze overlaid with filler while the exposed gauze is not so twisted. The resulting sheet of material 24 thus comprises a ply of filler sandwiched between two plies of gauze.

From rollers 18 the composite material is passed through a pair of press rollers 22 and then into a spool 25. Subsequently, the material is fed to unshown lay up tables, cut to size and sewed as by the use of two stitching heads mounted on a lateral conveyor. In performing this a handle 26 may be attached to a corner of an individual pad as shown in FIG. 1. Here also the stitch pattern may be seen to comprise a rectangular stitch 30 located peripherally about a central cross stitch pattern 32. After the sewing operation is completed, individual sponges are delinted by vacuuming and then inspected. The individual sponges are then folded, packaged and sterilized as with the use of ethylene oxide. If desired, one or more of the edges of each sponge may be tucked in prior to sewing to present a soft, flexible peripheral edge.

Laparotomy sponges of the type just described have been found to have enhanced absorbency over those of the prior art without a loss in tensile strength sufficient to cause the sponge to come apart in use. The sponge is substantially lint-free diminishing the possibility of lint caused infections from occuring in the area of sponge use. The absence of chemical binders also reduces the chance for skin discolorations from occuring as well as reduced cost in sponge manufacture. That the filler material is unwoven provides a further cost savings in manufacture.

In performing absorbency tests on the sponge just described, five specimens weighing 1 ± 0.05 grams each were placed in a copper wire basket weighing 3.13 grams. The loaded baskets were then completely submerged in water for 5 seconds at 25° ± 1° C, emerged and permitted to drip for ten seconds, and weighed. The cumulative weight of water absorbed totalled 44.85 grams. When five 100% cotton gauze laparotomy sponges were subjected to this same test, they were found to absorb 40.41 grams of water.

A Draize repeated insult test was also performed on the above described sponge. Here, ten human subjects were randomly selected to be exposed to eleven sponges measuring one inch square each. The upper portion of the inner arm was chosen as the sponge site due to its relatively high degree of skin sensitivity. The sponges were moistened with distilled water and held in place by a cellophane coverlet to aid in retardation of any possible volatile substances. A 24 hour contact period was followed by an examination of the site. No skin difference in color was found to exist between the sponge covered and surrounding skin sites. Test repeat following a 24 hour rest period was also observed to result in no apparent skin irritation.

It should be understood that the just described embodiment merely illustrates principles of the invention in one preferred form. Many modifications may, of course, be made to the specific construction and materials of the illustrated and described sponge, without departure from the spirit and scope of the invention as set forth by the following claims.

What is claimed is:

1. A laparotomy sponge comprising a filler consisting essentially of rayon and polypropylene fibers mixed together in a weight ratio of approximately 80% rayon and 20% polypropylene and shaped into a configuration having a waffled surface; and a foraminous cover secured about said filler.

2. A laparotomy sponge in accordance with claim 1 wherein said rayon and polypropylene fibers are heat bonded together.

3. A laparotomy sponge in accordance with claim 1 wherein said filler has opposing surfaces, each having a waffled configuration of alternate raised and depressed areas.

4. A laparotomy sponge in accordance with claim 1 wherein said waffled configuration is of a diamond pattern.

5. A laparotomy sponge in accordance with claim 1 wherein said central ply comprises rayon fibers heat bonded to polypropylene fibers.

6. A laparotomy sponge in accordance with claim 1 wherein said filler is a central ply and has a weight of 45–55 grams per square yard.

* * * * *